(12) United States Patent
Deng et al.

(10) Patent No.: US 9,936,930 B2
(45) Date of Patent: Apr. 10, 2018

(54) METHOD AND APPARATUS FOR DETERMINING TREATMENT MARGIN OF TARGET AREA

(71) Applicant: SIEMENS AKTIENGESELLSCHAFT, Munich (DE)

(72) Inventors: Xiang Deng, Beijing (CN); Jie Zheng, Beijing (CN)

(73) Assignee: Siemens Aktiengesellschaft, München (DE)

(*) Notice: Subject to any disclaimer, the term of this patent is extended or adjusted under 35 U.S.C. 154(b) by 168 days.

(21) Appl. No.: 14/013,188

(22) Filed: Aug. 29, 2013

(65) Prior Publication Data

US 2014/0064449 A1 Mar. 6, 2014

(30) Foreign Application Priority Data

Aug. 31, 2012 (CN) .......................... 2012 1 0320819

(51) Int. Cl.
*A61B 6/00* (2006.01)
*A61B 6/03* (2006.01)

(52) U.S. Cl.
CPC .............. *A61B 6/504* (2013.01); *A61B 6/032* (2013.01); *A61B 6/4441* (2013.01);
(Continued)

(58) Field of Classification Search
CPC ..... A61B 6/504; A61B 6/5235; A61B 6/5217; A61B 6/4441
See application file for complete search history.

(56) References Cited

U.S. PATENT DOCUMENTS 7,876,939 B2* 1/2011 Yankelevitz et al. ......... 382/128
2007/0100226 A1 5/2007 Yankelevitz et al.
2009/0287066 A1* 11/2009 Meissner et al. ............. 600/300

FOREIGN PATENT DOCUMENTS

CN 102393959 A 3/2012
CN 102548478 A 7/2012
(Continued)

OTHER PUBLICATIONS

Iyer, Ramesh S. et al.: "Image Fusion as a New Postprocessing Method to Evaluate the Radiofrequency Ablation Zone After Treatment of Malignant Liver Tumors", in: Journal of Assisted Tomography, 2010, vol. 34, No. 2, pp. 226-228.
(Continued)

*Primary Examiner* — Dani Fox
(74) *Attorney, Agent, or Firm* — Lempia Summerfield Katz LLC

(57) ABSTRACT

Disclosed is a method and apparatus for determining a tumor ablation margin. The method includes acquiring an angiography image before tumor ablation and an angiography image after tumor ablation when tumor ablation is performed, registering the angiography image before tumor ablation and the angiography image after tumor ablation, and determining the tumor ablation margin according to the relative positions of the tumor area in the angiography image before tumor ablation and the ablation area in the angiography image after tumor ablation after registration. Using an embodiment, one directly determines the tumor ablation margin during tumor ablation, thus improving the efficiency and success rate of tumor ablation.

18 Claims, 4 Drawing Sheets

(52) U.S. Cl.
CPC .......... *A61B 6/5217* (2013.01); *A61B 6/5235* (2013.01); *A61B 6/463* (2013.01)

(56) References Cited

FOREIGN PATENT DOCUMENTS

| CN | 102609620 A | 7/2012 |
|---|---|---|
| CN | 102609621 A | 7/2012 |
| JP | 2000306104 A | 11/2000 |

OTHER PUBLICATIONS

Kim, Kyung Won et al.: "Safety Margin Assessment After Radiofrequency Ablation of the Liver Using Registration of Preprocedure and Postprocedure CT Images", in: AJR 2011; vol. 196; pp. W565-W572; DOI:10.2214/AJR.10.5122.

\* cited by examiner

```
┌─────────────────────────────────────────────────────────────────┐
│  Acquiring an angiography image before tumor ablation and an    │
│  angiography image after tumor ablation when tumor ablation is  │
│  performed                                                       │
│                            11                                    │
└─────────────────────────────────────────────────────────────────┘
                                │
                                ▼
┌─────────────────────────────────────────────────────────────────┐
│  Registering the angiography image before tumor ablation and    │
│  the angiography image after tumor ablation                      │
│                            12                                    │
└─────────────────────────────────────────────────────────────────┘
                                │
                                ▼
┌─────────────────────────────────────────────────────────────────┐
│  Determining a tumor ablation margin according to the relative   │
│  positions of the tumor area in the angiography image before    │
│  tumor ablation and the ablation area in the angiography image   │
│  after tumor ablation after registration                         │
│                            13                                    │
└─────────────────────────────────────────────────────────────────┘
```

*Fig. 1*

```
┌─────────────────────────────────────────────────────────────────┐
│  Acquiring a 3D Dyna CT image before tumor ablation and          │
│  identifying the boundary of the tumor area therein              │
│                            21                                    │
└─────────────────────────────────────────────────────────────────┘
                                │
                                ▼
┌─────────────────────────────────────────────────────────────────┐
│  Acquiring a 3D Dyna CT image after tumor ablation and           │
│  identifying the boundary of the ablation area therein           │
│                            22                                    │
└─────────────────────────────────────────────────────────────────┘
                                │
                                ▼
┌─────────────────────────────────────────────────────────────────┐
│  Registering the 3D Dyna CT image before tumor ablation and the  │
│  3D Dyna CT image after tumor ablation                           │
│                            23                                    │
└─────────────────────────────────────────────────────────────────┘
                                │
                                ▼
┌─────────────────────────────────────────────────────────────────┐
│  Acquiring relative position data of the tumor area and the      │
│  ablation area                                                   │
│                            24                                    │
└─────────────────────────────────────────────────────────────────┘
                                │
                                ▼
┌─────────────────────────────────────────────────────────────────┐
│  Determining a quantitative tumor ablation margin according to   │
│  the relative position data of the tumor area and the ablation   │
│  area                                                            │
│                            25                                    │
└─────────────────────────────────────────────────────────────────┘
                                │
                                ▼
┌─────────────────────────────────────────────────────────────────┐
│  Displaying the tumor ablation margin through a pseudo color     │
│  image                                                           │
│                            26                                    │
└─────────────────────────────────────────────────────────────────┘
```

*Fig. 2*

METHOD AND APPARATUS FOR DETERMINING TREATMENT MARGIN OF TARGET AREA

CROSS REFERENCE TO RELATED APPLICATIONS

The present application claims priority to Chinese application No. 201210320819.7 CN filed Aug. 31, 2012, the entire content of which is hereby incorporated herein by reference.

TECHNICAL FIELD

The present invention relates to the technical field of target area treatment, and particularly, to a method and apparatus for determining a treatment margin of a target area.

BACKGROUND ART

At present, tumor ablation is a treatment option with minimum invasion against cancers. When tumor ablation is performed, the ablation area should have a proper size, thereby influencing normal tissues and structures surrounding the tumor as little as possible while destructing the entire tumor. Therefore, to have a proper margin between the tumor boundary and the boundary of the ablation area is the key to tumor ablation success.

In the prior art, the common way to determine a tumor ablation margin is to compare the pre-operative and post-operative computed tomography (CT) images, so as to confirm whether there is a proper margin between the pre-operative tumor area and the post-operative ablation area. In the above-mentioned manner, the post-operative CT image must be used; therefore, the determination and assessment of the tumor ablation margin can only be performed after the operation, and the tumor ablation margin cannot be determined during the operation. When the size of the ablation area is small, after this tumor ablation has been completed, tumor ablation needs to be performed again, until a proper tumor ablation margin is obtained, resulting in repeated tumor ablation surgeries against the same tumor.

SUMMARY OF THE INVENTION

An embodiment of the present invention provides a method and apparatus for determining a treatment margin of a target area, which are capable of directly determining the treatment margin of the target area during target area treatment.

The present invention provides a method for determining a treatment margin of a target area, comprising: acquiring a pre-treatment and post-treatment image of the target area, and segmenting out a pre-treatment and post-treatment boundary in said image; registering said pre-treatment and post-treatment image; and quantitatively determining a treatment margin of the target area according to the boundaries of said pre-treatment and post-treatment image after registration.

The present invention further provides an apparatus for determining a treatment margin of a target area, comprising: an image acquisition module for acquiring, on site, a pre-treatment and post-treatment image of the target area; an image segmentation module for segmenting out a pre-treatment and post-treatment boundary in said image; an image registration module for registering said pre-treatment and post-treatment image; and a margin determination module for determining a treatment margin of the target area according to the boundaries of said pre-treatment and post-treatment image after registration.

The present invention further provides an apparatus for determining a treatment margin of a target area, comprising: a memory for storing an executable instruction; and a processor for executing a step of the method according to the stored executable instruction.

The present invention further provides a machine readable medium storing a machine executable instruction thereon, wherein when said machine executable instruction is executed, the machine carries out a step of the method.

It can be seen that the method and apparatus for determining a treatment margin of a target area provided in an embodiment of the present invention have the following advantages;

First, the present invention can directly determine the quantitative treatment margin of the target area during target area treatment. Compared with the way of subjective assessment, i.e., qualitatively determining the treatment margin of the target area, the present invention is capable of avoiding the uncertainty caused by subjective factors, thereby significantly improving the accuracy of the result of target area treatment margin determination. Meanwhile, the present invention can carry out on-site assessment on the effect of a target area treatment in a timely manner, so that the target area treatment margin can be directly determined during the target area treatment, thus improving the efficiency and success rate of the target area treatment.

BRIEF DESCRIPTION OF THE DRAWINGS

FIG. 1 is a flow chart of a method for determining a tumor ablation margin in an embodiment of the present invention.

FIG. 2 is a flow chart of a method for determining a tumor ablation margin in another embodiment of the present invention.

DETAILED DESCRIPTION

Figure 3A:
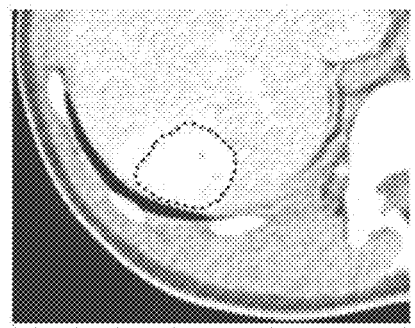
FIG. 3a is a schematic diagram of a tumor area segmented out from a C-arm angiography image before tumor ablation in an embodiment of the present invention.

In order to make the object, technical solutions and advantages of the present invention more clear, an embodiment of the present invention will be further described in detail hereinbelow by way of examples.

The present invention provides a method for determining a treatment margin of a target area, comprising: acquiring a pre-treatment and post-treatment image of the target area, and segmenting out a pre-treatment and post-treatment boundary in said image; registering said pre-treatment and post-treatment image; and quantitatively determining a treatment margin of the target area according to the boundaries of said pre-treatment and post-treatment image after registration. The present invention further provides an apparatus for determining a treatment margin of a target area, comprising: an image acquisition module for acquiring, on site, a pre-treatment and post-treatment image of the target area; an image segmentation module for segmenting out a pre-treatment and post-treatment boundary in said image; an image registration module for registering said pre-treatment and post-treatment image; and a margin determination module for determining a treatment margin of the target area according to the boundaries of said pre-treatment and post-treatment image after registration.

The following embodiment is an embodiment of determining a tumor ablation margin. However, it is noteworthy that the present invention is not limited to this embodiment, other interventional operations such as stent implantation in case of coronary artery stenosis, etc., and the field of other target areas of treatment may all use the apparatus and method provided in the present invention. The images of the present invention can also be acquired using other means widely known to a person skilled in the art.

FIG. 1 is a flow chart of a method for determining a tumor ablation margin in an embodiment of the present invention. As shown in FIG. 1, the method for determining a tumor ablation margin provided in an embodiment of the present invention comprises the following steps.

Step 11, acquiring an angiography image before tumor ablation and an angiography image after tumor ablation when tumor ablation is performed.

In an embodiment of the present invention, an angiography image can be acquired by means of angiography equipment, such as C-arm angiography equipment, running in the operating room during tumor ablation, wherein the angiography image can be a 2D or 3D angiography image. Preferably, the use of a 3D C-arm angiography image, such as a 3D Dyna CT image, can obtain the comprehensive relative positions of the tumor area and the ablation area, so as to determine the precise tumor ablation margin.

Step 12, registering the angiography image before tumor ablation and the angiography image after tumor ablation.

During tumor ablation, the breath or other factors of a patient will cause the position of the body or an organ of the patient to change; therefore, angiography images before tumor ablation and after tumor ablation need to be registered, in order to ensure that the right relative positions of the tumor area and the ablation area are obtained.

Step 13, determining a tumor ablation margin according to the relative positions of the tumor area in the angiography image before tumor ablation and the ablation area in the angiography image after tumor ablation after registration.

In this step, the registration results can be used to convert the angiography image before tumor ablation or the angiography image after tumor ablation, thereby obtaining the accurate relative positions of the tumor area and the ablation area. The tumor ablation margin is determined according to the relative positions of the tumor area and the ablation area. Specifically, the tumor ablation margin can be qualitatively determined by displaying the relative positions of the tumor area and the ablation area. According to the qualitatively determined tumor ablation margin, an interventional radiologist can subjectively assess whether the tumor ablation margin is proper and whether the tumor ablation needs to be continued.

In an embodiment of the present invention, after the tumor ablation margin is determined, the tumor ablation margin can be provided to the interventional radiologist in a variety of ways, such as displaying the images of the tumor area and the ablation area, displaying the image of the tumor ablation margin, broadcasting the position range of the tumor ablation margin, and so on.

Thus, the method for determining a tumor ablation margin in an embodiment of the present invention is capable of directly determining a tumor ablation margin during tumor ablation, and if no proper tumor ablation margin is acquired, this tumor ablation can be continued until the proper tumor ablation margin is acquired. Since it is not required to wait for post-operative CT scan results, repeated operations caused by improper tumor ablation margin is effectively avoided, and the efficiency and success rate of tumor ablation operations are significantly increased.

According to an embodiment of the present invention, a quantitative tumor ablation margin can also be determined according to the relative positions of the tumor area and the ablation area after registration.

Specifically, the boundary of the tumor area is segmented out in the angiography image before tumor ablation and the boundary of the ablation area is segmented out in the angiography image after tumor ablation, and after registration, relative position data of the tumor area and the ablation area is obtained according to the boundary of the tumor area and the boundary of the ablation area, and then a quantitative tumor ablation margin is determined according to the relative position data of the tumor area and the ablation area.

Preferably, the boundary of the tumor area and the ablation area can be segmented out on the original image before registration, so as to avoid boundary segmentation on the image after registration, thereby avoiding error superposition caused by boundary segmentation after registration.

Thus, according to an embodiment of the present invention, a quantitative tumor ablation margin can also be directly determined during tumor ablation. Compared with qualitatively determining a tumor ablation margin using a subjective assessment method, this can avoid the uncertainty caused by subjective factors, thereby significantly enhancing the accuracy of the result of tumor ablation margin determination.

Taking the C-arm angiography image being a 3D Dyna CT image as an example, the method for determining a quantitative tumor ablation margin in an embodiment of the present invention will be described in detail below.

FIG. 2 is a flow chart of a method for determining a tumor ablation margin in another embodiment of the present invention. As shown in FIG. 2, the method for determining a tumor ablation margin provided in an embodiment of the present invention comprises the following steps.

Step 21, acquiring a 3D Dyna CT image before tumor ablation and segmenting out the boundary of the tumor area therein.

In this step, the 3D Dyna CT image before tumor ablation stored in 3D C-arm angiography equipment can be directly downloaded, and the tumor area in the 3D Dyna CT image can be segmented out through a semi-automatic segmentation algorithm, to obtain the boundary of the tumor area, thus facilitating subsequent image processing as well as facilitating viewing of the position of the tumor area by the interventional radiologist. It is noteworthy that other segmentation algorithms can also be used to segment out boundaries and even the method of manual labeling can be used to segment out boundaries. The present invention does not impose any restrictions thereon.

FIG. 3a shows a tumor area segmented out in a 3D Dyna CT image before tumor ablation, wherein the boundaries of the tumor area are represented with dotted lines.

Step 22, acquiring a 3D Dyna CT image after tumor ablation and segmenting out the boundary of the ablation area therein.

In operation, after tumor ablation, the current 3D Dyna CT image after tumor ablation is acquired and the ablation area in the 3D Dyna CT image is segmented out through a semi-automatic segmentation algorithm, to obtain the boundary of the ablation area, thus facilitating subsequent image processing as well as facilitating the viewing of the position of the ablation area by the interventional radiologist.

Figure 3B:
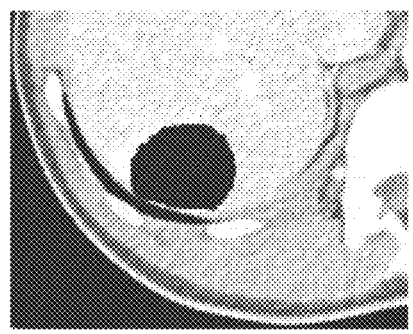
FIG. 3b is a schematic diagram of an ablation area segmented out from a C-arm angiography image after tumor ablation in an embodiment of the present invention.

FIG. 3b shows an ablation area segmented out in the 3D Dyna CT image after tumor ablation, wherein the approximate circular shadow area is the ablation area and the boundary of the shadow area is the boundary of the ablation area.

Step 23, registering the 3D Dyna CT image before tumor ablation and the 3D Dyna CT image after tumor ablation.

In this step, existing image registration methods can be used, preferably non-rigid image registration methods, to registrate the two 3D Dyna CT images, i.e. the 3D Dyna CT image before tumor ablation and the 3D Dyna CT image after ablation, so as to obtain the transformation from the 3D Dyna CT image before tumor ablation to the 3D Dyna CT image after ablation. A person skilled in the art should understand that, an embodiment of the present invention may also use other existing image registration algorithms, and the present invention does not impose restrictions thereon.

Step 24, acquiring relative position data of the tumor area and the ablation area.

In this step, the coordinate transformation result obtained through the registration algorithm can be used to acquire the relative position data of the tumor area and the ablation area.

Specifically, the boundary of the tumor area after registration is obtained according to the boundary of the tumor area obtained in step 21 and the coordinate transformation result obtained in step 23, and is then compared with the boundary of the ablation area obtained in step 22, to obtain the accurate relative position data of the tumor area and the ablation area.

Since the boundary of the tumor area is segmented out on the original image before registration, and the boundary of the tumor area after registration is calculated from the coordinate transformation result and the boundary of the tumor area before registration, it is not required to perform image segmentation on the image after registration and then segment out the boundary of the tumor area, thus avoiding the superposition of registration errors and image segmentation errors, and making the position of the tumor area and the position of the ablation area more accurate.

In addition, in this step the boundary of the ablation area after registration can also be obtained according to the boundary of the ablation area obtained in step 22 and the coordinate transformation result obtained in step 23, and then be compared with the boundary of the tumor area obtained in step 21, to obtain the accurate relative position data of the tumor area and the ablation area.

Step 25, determining a quantitative tumor ablation margin according to the relative position data of the tumor area and the ablation area.

In this step, it is possible to first acquire the surface distance between the tumor area and the ablation area according to the relative position data of the tumor area and the ablation area, and then determine the quantitative tumor ablation margin according to the surface distance between the tumor area and the ablation area.

Since the tumor area and the ablation area are both 3D Dyna CT images in this embodiment, the relative positions of the tumor area and the ablation area can be comprehensively obtained, providing interventional radiologists with accurate and adequate basis for judgment.

Step 26, displaying the tumor ablation margin through a pseudo color image.

In this step, the tumor ablation margin obtained in step 25 is displayed through a pseudo color image. In an embodiment of the present invention, it is also possible to use other methods to display the tumor ablation margin. Displaying through the pseudo color image is only a preferred example and is not intended to limit the protection scope of the present invention.

Figure 3C:
FIG. 3c is a schematic diagram of a tumor ablation margin in an embodiment of the present invention.

As shown in FIG. 3c. FIG. 3c shows the tumor area and the ablation area only, which intuitively shows the tumor ablation margin.

When an embodiment of the present invention is applied, other methods can also be used to provide a quantitative tumor ablation margin. For example, the distribution of values of the tumor ablation margin or the average value of the tumor ablation margin is shown in schematic diagrams, and so on.

In an embodiment of the present invention, a user can select the required C-arm angiography image from the saved images, thereby carrying out semi-automatic tumor ablation. Specifically, the user can specify the required part of area from the required C-arm angiography image, for example specifying an area near the tumor through devices such as a mouse or a touch screen, etc. In the subsequent operations, the treatment as described in the above-mentioned steps 21-26 is performed on the part of the area specified by the user only, so as to reduce the burden of data processing.

As can be seen, according to this embodiment, the tumor ablation margin can be directly determined during tumor ablation, and if no proper tumor margin ablation is obtained, this tumor ablation can be continued until a proper tumor ablation margin is obtained. Since it is not required to wait for post-operative CT scan results, repeated operations caused by improper tumor ablation margin are effectively avoided, and the efficiency and success rate of tumor ablation operations are significantly increased. Moreover, the quantitative tumor ablation margin can be determined in the embodiment, thus avoiding the uncertainty caused by subjective factors, and significantly improving the accuracy of the result of tumor ablation margin determination.

Figure 4:
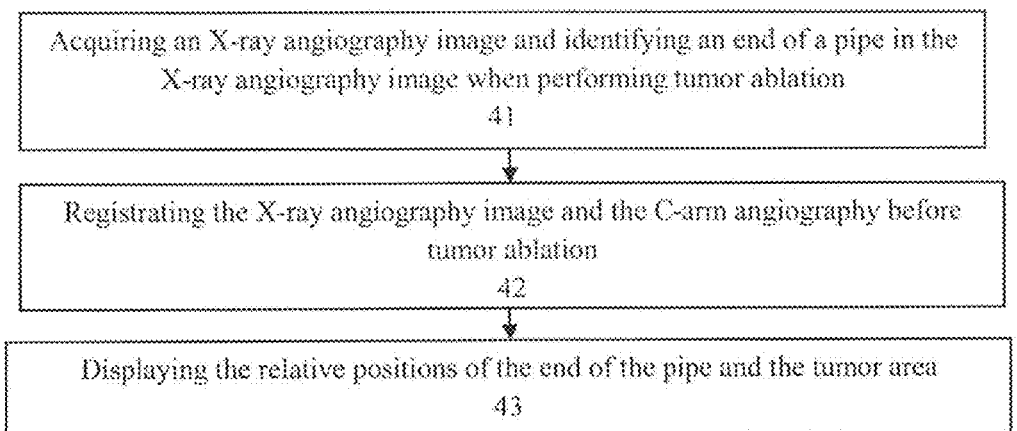
FIG. 4 is a flow chart of obtaining the relative positions of an end of a pipe and a tumor area in an embodiment of the present invention.

In order to achieve better tumor ablation effect, according to an embodiment of the present invention, the relative positions of the end of the tumor ablation pipe and the tumor area can also be provided in real time during a tumor ablation operation, so as to guide the tumor ablation operation. FIG. 4 is a flow chart of obtaining the relative positions of an end of a pipe and a tumor area in an embodiment of the present invention. As shown in FIG. 4, the flow specifically comprises the following steps.

step 41, acquiring an X-ray angiography image of a tumor ablation intervention pipe and displaying an end of the pipe in the X-ray angiography image when tumor ablation is performed.

In this embodiment, the X-ray angiography image is a 2D X-ray angiography image. In practical applications, other types of images which are capable of displaying the end of the pipe can also be used.

In this step, the position of the end of the pipe in the 2D X-ray angiography image can be obtained through an automatic image segmentation algorithm. It is noteworthy that the position of the end of the pipe in the X-ray angiography image can also be provided by using other segmentation algorithms such as a semi-automatic image segmentation algorithm, etc. The present invention does not impose any restrictions thereon.

Step 42, registering the X-ray angiography image and the 3D Dyna CT image before tumor ablation.

In this step, a transformation matrix is obtained using an automatic 2D-3D registration algorithm, which registers the 3D Dyna CT image before tumor ablation to the X-ray angiography image.

Step 43, displaying the relative positions of the end of the pipe and the tumor area.

Figure 5:
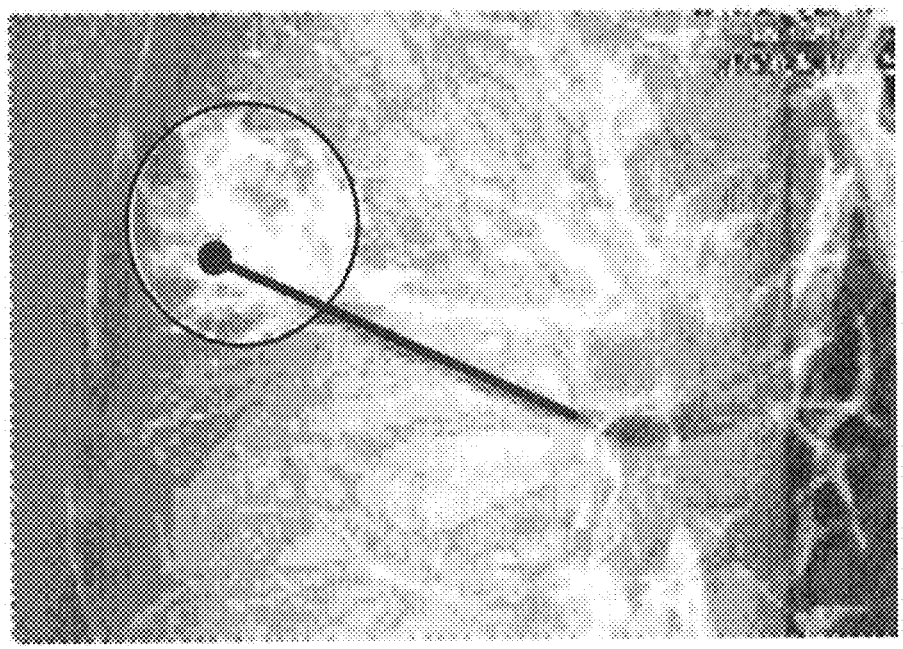
FIG. 5 is a schematic diagram of obtaining the relative positions of an end of a pipe and a tumor area in an embodiment of the present invention.

The relative positions of the end of the pipe and the tumor area are displayed in the registered image. FIG. 5 is a schematic diagram of obtaining the relative positions of an end of a pipe and a tumor area in an embodiment of the present invention.

It can be seen that by registering the end of the pipe with the 3D Dyna CT image before tumor ablation, the accurate relative positions between the end of the intervention pipe performing tumor ablation and the tumor area can be obtained, so as to provide accurate reference for the conduction of tumor ablation, thus improving the accuracy and efficiency of tumor ablation, facilitating precise tumor ablation during an operation, and reaching proper tumor ablation margin.

Figure 6:
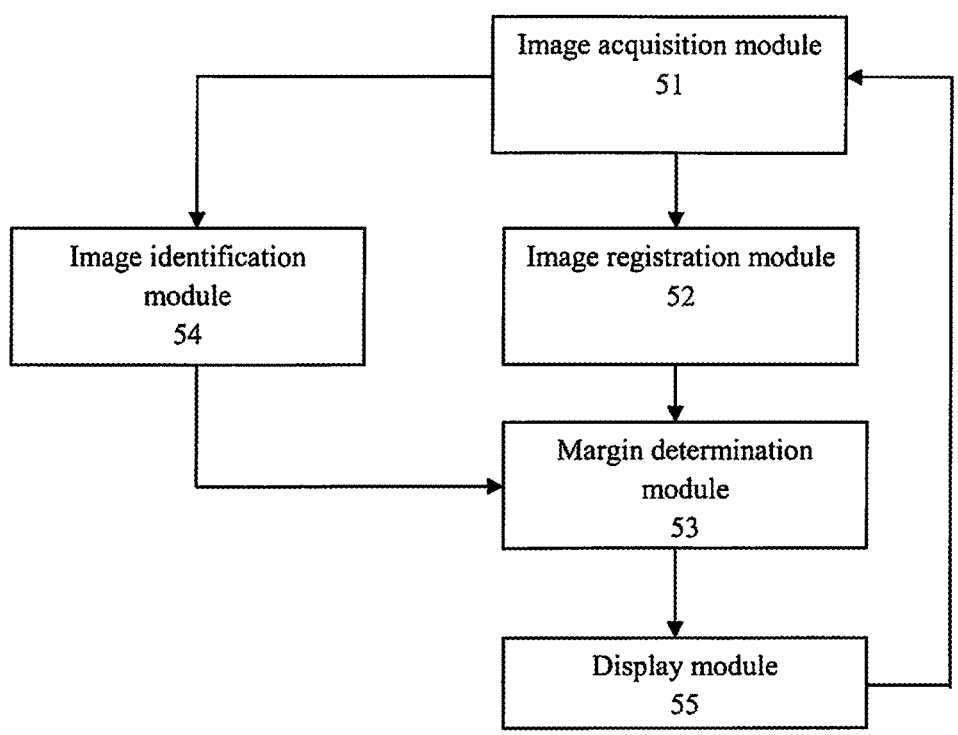
FIG. 6 is a structural schematic diagram of an apparatus for determining a tumor ablation margin in an embodiment of the present invention.

Based on the above-mentioned method for determining a tumor ablation margin, an embodiment of the present invention also provides an apparatus for determining a tumor ablation margin. FIG. 6 shows a structural schematic diagram of an apparatus for determining a tumor ablation margin in an embodiment of the present invention. As shown in FIG. 6, the apparatus comprises an image acquisition module 51, an image registration module 52 and a margin determination module 53.

The image acquisition module 51 is used for acquiring an angiography image before tumor ablation and an angiography image after tumor ablation when tumor ablation is performed; the image registration module 52 is used for registering the angiography image before tumor ablation and the angiography image after tumor ablation; and the margin determination module 53 is used for determining a tumor ablation margin according to the relative positions of a tumor area in the angiography image before tumor ablation and an ablation area in the angiography image after tumor ablation after registration.

In an embodiment of the present invention, an angiography image can be acquired by means of angiography equipment, such as C-arm angiography equipment, running in the operating room during tumor ablation, wherein the angiography image can be a 2D or 3D angiography image. Preferably, the use of a 3D C-arm angiography image, such as a 3D Dyna CT image, can obtain the comprehensive relative positions of the tumor area and the ablation area, so as to determine the precise tumor ablation margin.

In addition, according to an embodiment of the present invention, the apparatus for acquiring tumor ablation margin further comprises an image segmentation module 54; the image segmentation module 54 is used for segmenting out the boundary of the tumor area in the angiography image before tumor ablation and segmenting out the boundary of the ablation area in the angiography image after tumor ablation. Accordingly, the margin determination module 53 is further used for acquiring the relative position data of the tumor area and the ablation area according to the boundary of the tumor area, the boundary of the ablation area and the coordinate transformation result output by the image registration module 52, and for determining the quantitative tumor ablation margin according to the relative position of the tumor area and the ablation area.

In an embodiment of the present invention, the apparatus for determining a tumor ablation margin further comprises: a display module 55 for displaying the determined tumor ablation margin through a pseudo color image. In practical applications, the display module 55 can also be used to display the segmented-out ablation area and tumor area, for easy viewing by the user.

Furthermore, the display module 55 can also display for the user the angiography image before tumor ablation and the angiography image after tumor ablation, and receive the part specified by the user in the angiography image before tumor ablation, and take it as the angiography image before tumor ablation; and receive the part specified by the user in the angiography image after tumor ablation, and take it as the angiography image after tumor ablation. In the subsequent operations for determining the tumor ablation margin, the above-mentioned module only processes the part of area selected by the user, thus reducing the burden of data processing.

Thus, the apparatus for determining a tumor ablation margin in an embodiment of the present invention can be directly used in the operating room during tumor ablation and is capable of directly determining the tumor ablation margin, and if no proper tumor ablation margin is acquired, this tumor ablation can be continued until a proper tumor ablation margin is acquired. Since it is not required to wait for post-operative CT scan results, repeated operations caused by an improper tumor ablation margin is effectively avoided, and the efficiency and success rate of tumor ablation operations are significantly increased. Moreover, the apparatus for determining a tumor ablation margin in an embodiment of the present invention is capable of determining a quantitative tumor ablation margin, thus avoiding the uncertainty caused by subjective factors and significantly improving the accuracy of the result of tumor ablation margin determination.

In an embodiment of the present invention, the image acquisition module 51 is further used for acquiring an X-ray angiography image of a tumor ablation intervention pipe when tumor ablation is performed, and the image segmentation module is further used for providing an end of the intervention pipe in the X-ray angiography image; accordingly, the image registration module 52 is further used for registering the X-ray angiography image and the angiography image before tumor ablation; and the display module 55 is further used for displaying the relative positions of the end of the pipe and said tumor area. Therefore, providing the relative positions of the end of the tumor ablation intervention pipe and the tumor area during a tumor ablation operation facilitates precise tumor ablation during the operation and achieves an appropriate tumor ablation margin.

The hardware architecture composition of the apparatus for determining a tumor ablation margin in an embodiment of the present invention is described below. The apparatus comprises a processor, a memory, and an image processing chip.

The memory is used for storing an angiography image before tumor ablation and an angiography image after tumor ablation, and is further used for storing an instruction code, and the operations accomplished when the instruction code is executed are mainly the functions accomplished by the margin determination module in the above-mentioned tumor ablation margin apparatus, which will not be redundantly described here.

The image processing chip is used for communicating with the memory, reading the angiography image before tumor ablation and the angiography image after tumor ablation, and processing these images so as to accomplish the functions of the image registration module in the above-mentioned apparatus for determining a tumor ablation margin, which will not be described here superfluously.

The processor is used for communicating with the memory, sending the angiography image before tumor ablation and the angiography image after tumor ablation obtained through an interface to the memory, and accomplishing the functions of the image acquisition module in the above-mentioned apparatus for determining a tumor ablation margin; and is also used for reading and executing the instruction code stored in the memory, and communicating with the image processing chip, and accomplishing the functions accomplished by the margin determination module in the above-mentioned apparatus for determining a tumor ablation margin, which will not be described here superfluously.

What are mentioned above are merely the preferred embodiments of the present invention, and they are not intended to limit the protection scope of the present invention. Suitable modifications can be made to the preferred embodiments of the present invention in the particular implementation process, to adapt to the specific needs of specific situations. Therefore, it can be understood that the particular embodiments of the present invention described herein are only role models and are not intended to limit the protection scope of the present invention.

We claim:

1. A method for determining a treatment margin of a target area, the method comprising:
    acquiring a pre-treatment image of the target area having a tumor;
    acquiring a post-treatment image of the target area in which the target area has been ablated;
    segmenting out a pre-treatment boundary in the pre-treatment image, wherein the pre-treatment boundary is a boundary of a tumor area;
    segmenting out a post-treatment boundary in the post-treatment image prior to registering the pre-treatment image and the post-treatment image, wherein the post-treatment boundary is a boundary of an ablation area, wherein the ablation area is configured to be greater than the tumor area, and wherein segmenting out the pre-treatment boundary and the post-treatment boundary prior to registration avoids superposition of registration errors and image segmentation errors;
    registering the pre-treatment image and the post-treatment image; and
    quantitatively determining a treatment margin of the target area according to the boundaries of the pre-treatment image and the post-treatment image after registration, wherein the treatment margin is a tumor ablation margin.

2. The method as claimed in claim 1, further comprising:
    providing positions of an end of a pipe for treating the target area, the providing of the positions comprising:
       acquiring an X-ray angiography image in real time and providing a position of the target area treatment pipe end in the X-ray angiography image;
       registering the X-ray angiography image and the angiography image of the target area before treatment; and
       displaying the positions of the target area treatment pipe end and the target area.

3. The method as claimed in claim 1, further comprising: displaying the target area treatment margin.

4. The method as claimed in claim 1, wherein:
    the pre-treatment image of the target area is a first portion specified by a user in the pretreatment image of the target area; and
    the post-treatment image of the target area is a second portion specified by the user in the post-treatment image of the target area.

5. The method as claimed in claim 1, wherein the pre-treatment image and the post-treatment image is a 3D C-arm angiography image.

6. The method of claim 1, wherein quantitatively determining a treatment margin of the target area involves comparing the segmented pre-treatment boundary and a coordinate transformation result obtained after registration to the segmented post-treatment boundary.

7. The method of claim 1, wherein the tumor ablation margin is a surface distance between the pre-treatment boundary and the post-treatment boundary.

8. The method of claim 1, further comprising:
    determining whether the tumor ablation margin is proper such that the tumor has been effectively ablated.

9. The method of claim 8, further comprising:
    repeating the acquiring of pre-treatment and post-treatment images, segmenting of pre-treatment and post-treatment boundaries, registering of the pre-treatment and post-treatment images, and quantitatively determining the treatment margin until the tumor ablation margin is determined to be proper.

10. An apparatus for determining a treatment margin of a target area, comprising:
    an image acquisition module for acquiring, on site, a pre-treatment image of the target area having a tumor and a posttreatment image of the target area in which the target area has been ablated;
    an image segmentation module for segmenting out a pre-treatment boundary in the pre-treatment image and a post-treatment boundary in the post-treatment image prior to registration, wherein the pre-treatment boundary is a boundary of a tumor area and the post-treatment boundary is a boundary of an ablation area, wherein the ablation area is configured to be greater than the tumor area, and wherein segmenting out the pre-treatment boundary and the post-treatment boundary prior to registration avoids superposition of registration errors and image segmentation errors;
    an image registration module for registering the pre-treatment image and the post-treatment image; and
    a margin determination module for determining a treatment margin of the target area according to the boundaries of the pre-treatment image and the post-treatment image after registration, wherein the treatment margin is a tumor ablation margin.

11. The apparatus as claimed in claim 10, further comprising a display module for displaying the target area treatment margin.

12. The apparatus as claimed in claim 10, wherein,
    the image acquisition module is further used for acquiring an X-ray angiography image of a pipe for treating the target area;

the image segmentation module is further used for providing the position of an end of the pipe for treating the target area in the X-ray angiography image; and the image registration module is further used for registering the X-ray angiography image and the pre-treatment angiography image of the target area.

13. The apparatus as claimed in claim 12, further comprising a display module for displaying the positions of the target area treatment pipe end and the target area.

14. The apparatus as claimed in claim 10, wherein,
the pre-treatment image of the target area is a first portion specified by a user in the pre-treatment image of the target area; and
the post-treatment image of the target area is a second portion specified by the user in the post-treatment image of the target area.

15. The apparatus as claimed in claim 10, wherein the pre-treatment and post-treatment image is a 3D C-arm angiography image.

16. The apparatus of claim 10, wherein the margin determination module for determining a treatment margin compares the segmented pre-treatment boundary and a coordinate transformation result obtained after registration to the segmented post-treatment boundary.

17. The apparatus of claim 10, wherein the tumor ablation margin is a surface distance between the pre-treatment boundary and the post-treatment boundary.

18. An apparatus for determining a treatment margin of a target area, the apparatus comprising:

a memory for storing an executable instruction; and
a processor configured to execute, in the stored executable instruction, at least the following:
acquire a pre-treatment image of the target area having a tumor;
acquire a post-treatment image of the target area in which the target area has been ablated;
segment out a pre-treatment boundary in the pre-treatment image, wherein the pre-treatment boundary is a boundary of a tumor area;
segment out a post-treatment boundary in the post-treatment image prior to registering the pre-treatment image and the post-treatment image, wherein the post-treatment boundary is a boundary of an ablation area, wherein the ablation area is configured to be greater than the tumor area, and wherein segmenting out the pre-treatment boundary and the post-treatment boundary prior to registration avoids superposition of registration errors and image segmentation errors;
register the pre-treatment image and the post-treatment image; and
quantitatively determine a treatment margin of the target area according to the boundaries of the pre-treatment image and the post-treatment image after registration, wherein the treatment margin is a tumor ablation margin.

* * * * *